(12) United States Patent
Löfqvist et al.

(10) Patent No.: US 6,395,775 B1
(45) Date of Patent: May 28, 2002

(54) COMBATING PEST INSECTS

(76) Inventors: Jan Löfqvist, Vallby 16, 245 92 Staffanstorp; Marie Bengtsson; Peter Witzgall, both of Iliongränden 0228, 224 71 Lund, all of (SE)

( * ) Notice: Subject to any disclaimer, the term of this patent is extended or adjusted under 35 U.S.C. 154(b) by 0 days.

(21) Appl. No.: 09/635,749

(22) Filed: Aug. 10, 2000

Related U.S. Application Data

(63) Continuation-in-part of application No. 08/894,955, filed as application No. PCT/SE96/00275 on Mar. 4, 1996.

(30) Foreign Application Priority Data

Mar. 3, 1995  (SE) ............................................... 9500774

(51) Int. Cl.⁷ ............................................... A01N 31/02

(52) U.S. Cl. ..................... 514/513; 514/693; 514/842; 514/957

(58) Field of Search ................................ 514/513, 693, 514/842, 957

(56) References Cited

U.S. PATENT DOCUMENTS

| | | | |
|---|---|---|---|
| 3,852,419 A | 12/1974 | Roelofs et al. | 514/739 |
| 4,323,556 A | 4/1982 | Dal Moro et al. | 424/84 |
| 4,734,281 A | 3/1988 | Yamamoto et al. | 424/408 |
| 5,599,848 A | * 2/1997 | Klein et al. | 514/739 |

FOREIGN PATENT DOCUMENTS

| | | |
|---|---|---|
| EP | 236188 A1 | 9/1987 |
| WO | WO 883755 A1 | 6/1988 |

OTHER PUBLICATIONS

Roelofs et al., Science 174: 2970299 (1974)l.*
McDonough et al., J. Chem. Ecol. 22(3): 415–423 (1996).*
Hathaway, et al., Environ Entomol 8(2)318–321 (1979) Abstract.
Szanto et al., Acta Phytopathol Acad Sci Hung 14(3–4):461–464 (1979) Abstract.
Carde et al., Entomol Exp Appl 22(3):280–288 (1977) Abstract.
Hathaway, et al., J Entomol Soc B C 82(0):18–22 (1985) Abstract.
Arn, et al., Eperientia 30(10):1142–1144 (1974).
Zakatar, et al., Vestsi Akademii Navuk Belarusi, Seryya Biyalagichnykh Navuk 1:61–67 (1994) Abstract.
Kolesova et al., Zashch, rast. 5:24–26 (1982). Abstract.
Annual Review of Etomology, vol. 40, 1995, Ring T. Carde et al., "Control of Moth Pests by Mating Disruption: Successes and Constraintsʼʼ, p. 559–585, 576–579.
STN Internationak, File CAPLUS, CAPLUS accession No. 1986:202262, Einhorn, Jacques et al: "Secondary components of the codling moth (Cydia pomenella L.) (Lepidoptera, Tortricidae) sex pheromone. II. First results on the behavioral effects", C. R. Acad. Sci., Ser. 3 (1986), 302(7), 263–6.
STN International, File CAPLUS, CAPLUS accession No. 1975:52585, Hathaway, D.O. et al: "Inhibitor of sexual attaction of male codling moths to a synthetic sex pheromone and virgin females in traps", Environ. Entomol. (1974), 3(3) pp. 576–579.

* cited by examiner

Primary Examiner—Jean C. Witz
(74) Attorney, Agent, or Firm—Oppedahl & Larson LLP

(57) ABSTRACT

The present invention relates to the use of a sex pheromone, E8,E10-dodecadien-1-ol, in combination with one or more behavioral antagonists or behavioral synergists for control of codling moth by mating disruption or attraction & killing.

10 Claims, 2 Drawing Sheets

COMBATING PEST INSECTS

This application is a continuation-in-part of U.S. Pat. application Ser. No. 08/894,955, filed Sep. 10, 1997, which is the U.S. National Phase of International application No. PCT/SE96/00275, which are incorporated herein by reference.

BACKGROUND OF THE INVENTION

The present invention relates to the use of the sex pheromone, E8,E10-dodecadien-1-ol, codlemone, in combination with one or two behavioural antagonists and/or behavioural synegists for control of codling moth, *Cydia pomonella* (Lepidoptera, Tortricidea) in fruit orchards by mating disruption or male attraction.

Biological methods of controlling pest insects have been faced with great interest during later years and in particular the use of pheromones, i.e. species specific scent substances which animals, such as insects, use to communicate and which substances elicit a certain behaviour or a biological activity. For several years pheromones have been marketed for control of certain pest insects on a commercial basis. The advantage of using pheromones for this purpose is the very high selectivity and the very great environmental advantage. Contrary to chemical inhibiting agents such as insecticides, the activity of the pheromones is directed solely towards the insect species intended, and as pheromones are substances that appear naturally, they do not give rise to resistance problems. Pheromones are active in very small amounts and are biologically degradable. They are not toxic to any part of the ecological system.

Sex pheromones of butterflies (in particular night moths and torthricides) are the most well known sex pheromones. In one control method, the confusion method, the pheromone is spread from sources provided with a synthetic sex pheromone substance in such a way that the whole area will become reeking with the substance. The males will then not find the females to any greater extent. The method is efficient. The confusion method is currently commercial with regard to a dozen moth species (Cardé & Minks, 1955, Ridgway et al, 1990). The most important obstacles for a rapid development of the confusion technique are within the fields of biology and chemistry. One does simply not know how and why the confusion technique works.

The dominant hypothesis for the male pheromone attraction of the females was formulated in 1978 by Roelofs. It is called the threshold hypothesis and states that the complete and proportionally natural pheromone blend is always a better stimulus of the complete behaviour than any other blend of the components. It will also release the behaviour at lower concentrations than any other blend. The hypothesis has governed and still governs, in principle, all pheromone studies.

In a review of successful and commercial cases using confusion, Minks & Cardé conclude (1988): "the natural blend achieves disruption of mating at lower application rates than either partial or off-ratio blends".

A sex pheromone may consist of up to 10 different, but biosynthetically closely related substances (Baker, 1989). Different species within a family utilize different combinations of such a theme. The species separation can be strengthened by the fact that species A has specific sensory neurons for the main component of species B as well, but responds with a negative, escaping behaviour on such a signal. As an example, the pine sawflies (hymeropteran) of the family Diprionidae (Löfqvist, 1986) will be mentioned.

The main component of the sex pheromone of *Neodiprion sertifer* has three chiral carbon atoms. The substance can thus appear in eight different enantiomers. Only one of them is active as a sex attractant. Another one thereof is a very strong behaviour antagonist. Only 1–2% of this together with the attractant is enough to completely block the attraction.

The main component of the sex pheromone of the codling moth, E8,E10-dodecadien-1-ol was identified in 1971 by Roelofs et al. Several research groups then worked with the identification of the composition of the pheromone. A relatively complete composition was published by Einhorn et al (1984) and Arn et al (1985) Roelofs et al (1972) found that the EE-isomer of the geometric isomers was very attractive while the other three inhibited the attraction of the codling moth. The commercial product thus consequently consists of 99% EE-isomer.

Mating Disruption

Insects use sex pheromones to communicate for mating. Pheromones elicit strong behavioural reactions in minute amounts, they are species-specific and non-toxic. By permeating the atmosphere with synthetic pheromones, olfactory communication and mate-finding can be prevented.

The economic importance of pheromonal methods of insect control is increasing due to problems with registration of toxic insecticides, insect resistance, environmental problems and consumer attitudes. Among the advantages of using pheromones is their specificity, the fact that they are active in very low amounts, and that they are not known to be toxic to any part of the ecological system.

The mechanisms of mating disruption (confusion) are still largely unknown. Pheromones usually consist of a blend of several compounds, which are attractive to conspecific males, but unattractive or even repellent to males of other species (Cardé et al, 1977; Witzgall et al. 1996b). The addition of pheromone synergists and pheromone antagonists, i.e. positive and negative agonists enhance the male behavioural response.

Successful attempts to control moths (Lepidoptera) by mating disruption include both blends of the main pheromone compounds and pheromone antagonists, as well as blends of pheromone and pheromone synergists (Minks & Cardé 1988; Bengtsson et al. 1994). However, there are no known cases where the main compound alone has shown to be more efficient than blends of the main pheromone compound with synergists or antagonists.

Male Annihilation

Male attraction to point sources of pheromone is also used to control insects. These pheromone sources can be used in large-capacity traps, or can be formulated together with insecticides ("attract and kill"; Charmillot & Hofer 1997).

A more complete synthetic pheromone blend is more attractive and thus more efficient than less complete blends. With the attract and kill method, it is important to attract the males close enough to the poisoned bait to ensure contact. We have shown that more complete pheromone blends which come as close as possible to the calling female, are more efficient.

It is possible to control the codling moth, *Cydia pomonella*, by confusion using the sex pheromone E8,E10-dodecadien-1-ol in a combination with one or more behaviour antagonists (EP-A-0 820 226, WO96/27289). Suitable behaviour antagonists are one or more of the geometric isomers of delta8,delta10-dodecadien-1-yl acetate. Further, the codling moth can be attracted and killed using a behavioural synergist using one or more of the substances of the group Z8-dodecen-1-yl acetate, E8-dodecen-1-yl acetate, Z10-dodecen-1-yl acetate and E10dodecen-1-yl acetate, or a very small amount of the geometric isomer E8,E10-dodecadien-1-yl acetate, which is synergistic.

SUMMARY OF THE INVENTION

The present invention provides an efficient method for controlling codling moths, *Cydia pomonella*, in fruit orchards by mating disruption or by attraction and killing, comprising the step of exposing the moths to E8,E10-dodecadien-1-ol in combination with one or more behavioral antagonists or behavioral synergists. Suitable behavioral antagonists include the geometric isomers of delta 8, delta 10-dodecadien-1-yl acetate. Suitable behavioral synergists include Z8-dodecen-1-yl acetate, E8-dodecen-1-yl acetate, Z10-dodecen-1-yl acetate and E10-dodecen-1-yl acetate, as well as a very small amount of the geometric isomer E8,E10-dodecadien-1-yl acetate, which is synergistic.

DETAILED DESCRIPTION OF THE INVENTION

The object of the present invention is to obtain an efficient method for controlling the codling moth in fruit orchards by utilizing the sex pheromone of said insect in combination with one or two behavioural antagonists.

It has now surprisingly been shown possible to be able to inhibit the codling moth, *Cydia pomonella*, by confusion by means of the use of the sex pheromone E8,E10-dodecadien-1-ol in a combination with one or more behavior antagonists.

The codling moth, *Cydia pomonella*, lives in habitate with a great number of other species. The competition in the communication channel using pheromones has led to the fact that the main component of the sex pheromone of one species simultaneously is a behaviour antagonist of another species. A number of such are known with regard to the codling moth, but the effect of them together with the sex pheromone has never been investigated. However, the confusion method based upon the own sex pheromone of the codling moth, has been developed into a commercial product (Charmillot, 1990; Pfeiffer, et al. 1993) which product, however, has a restricted use to low population densities and high amounts of compound.

The family Cydia consists of a great number of species. In many thereof, e.g. the pear moth, *Cydia pyrivora*, the main component of the sex pheromone is E8,E10-dodecadien-1-yl acetate, i.e. the same substance as of the codling moth, with the difference that the substance is present as an acetate ester, i.e. the end group is an acetate instead of an alcohol. It has turned out that the acetate is a behaviour antagonist of the codling moth, which is evident from the test results provided below.

Figure 1:
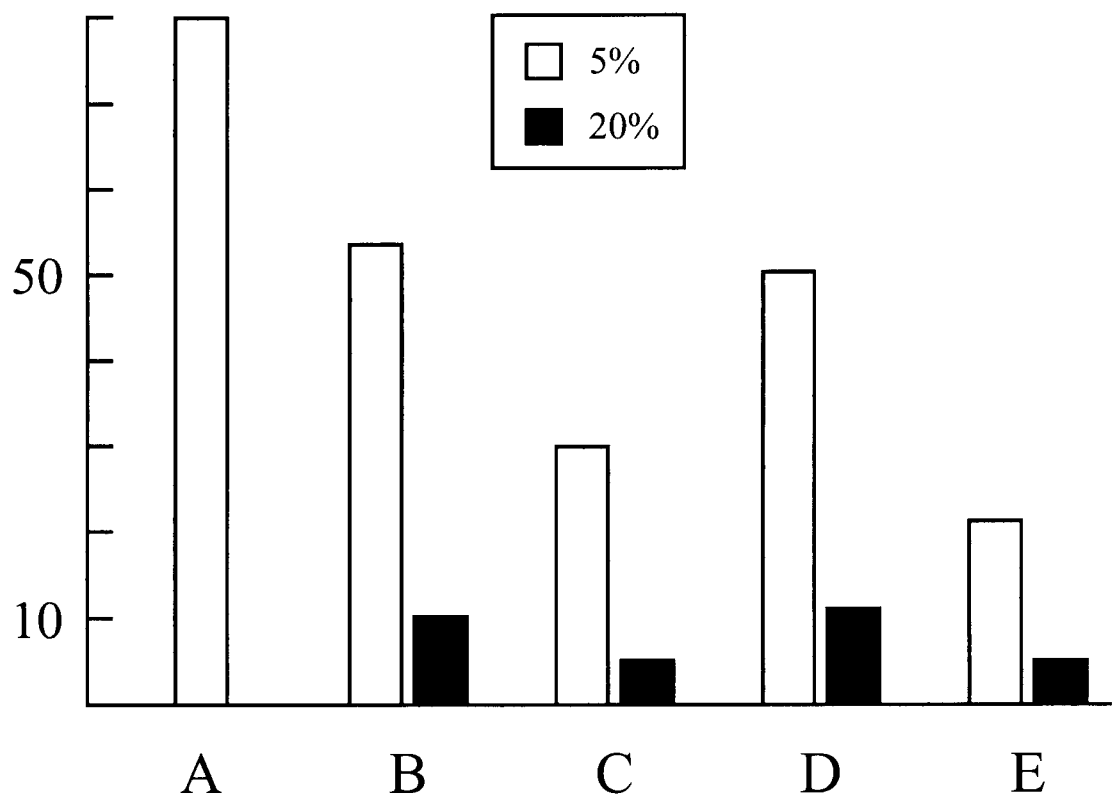
FIGS. 1A–1E show trapping results using the E8,E10-dodecadien-1-ol alcohol with and without the acetate for various isomers.

Pheromone traps were loaded with the pheromone, E8,E10-dodecadien-1-ol of the codling moth, (FIG. 1A). In other traps the alcohol was combined with the corresponding acetate (FIG. 1B). At a blend of 20% of the acetate the catch decreased to ⅛ (dark column). In further tests the other three isomers (EZ (FIGS. 1C, ZE (FIGS. 1D, and ZZ (FIG. 1E)) (FIGS. 1C–1E) were tested. They were all behaviour antagonists to the codling moth. The zz-isomer was the most powerful of the four isomers.

In another test a confusion test was carried out in 100 m² quadratic test areas in a fruit orchard. In each test four dispensing means, loaded with a behaviour antagonist, were placed in each of the four comers of the respective test area. In the respective center of each square, a pheromone trap loaded with the sex pheromone, E8, E10-dodecadien-1-ol of the codling moth, was placed. The confusing effect was calculated as the number of males trapped in the trap compared with the number trapped in a trap in a non-treated control square, i.e. without any behavior antagonist in the respective corner. Both the alcohol and the corresponding acetate had a strong confusing effect. However, the combination thereof had a clearly higher effect.

The sex pheromone of the codling moth, the alcohol, is as already mentioned, in commercial use. The inhibiting results are, however, not always satisfying, (Cardé & Minks, 1995, "Control of moth pests by mating disruption. Successes and constraints", Ann. Rev. Entomol. 49:559–585) in particular not in fruit orchards having high trees and a high population density. It has turned out that in such cases, the males are attracted to the tree tops. Probably, the concentration of pheromone from located dispensing means so low there, that the attracting power of the pheromone dominates its confusing effect. Males circulating in the tree tops may also be caught in lower placed traps which indicates a lacking confusing effect. However, if dispensing means in which the sex pheromone (the alcohol) is combined with a behavior antagonist (acetate) is placed out no males are observed flying around in the tree tops. Several of the males caught in pheromone traps in such treated squares can be seen flying some meters above the ground and straight into the trap. They never arrived from the top of the trees. The combination of the sex pheromone and a behavior antagonist can thus be regarded as a superior inhibiting method.

It has now been shown in wind tunnel experiments that small amounts of E8,Z10-dodeca-dien-1-ol and small amounts of E8,E10-dodecadienyl acetate enhances male attraction and close range behaviours at the pheromone source, compared to the main pheromone compound E8,E10-dodecadien-l-ol alone. The E8,E10-dodecadienyl acetate acts as an antagonist when present in high amounts, and as a synergist when present in lower amounts.

A two-component blend of 100 parts by weight E8,E10-dodecadien-1-ol and 3 parts by weight E8,Z10dodecadien-1-ol, and a two-component blend of 100 parts by weight E8,E10-dodecadien-1-ol and 1 part by weight E8,E10dodecadienyl acetate are more attractive than codlemone alone.

A rather complete account of the compounds produced by codling moth females, including E8,Z10-dodecadien-1-ol and E8,E10-dodecadienyl acetate has been published (Einhom et al. 1984; Arn et al. 1985). However, both compounds have previously been considered as pheromone antagonists (Hathaway et al. 1974; Witzgall et al. 1996a, El-Sayed et al. 1998).

Generally, pheromone antagonists are known to have a negative effect on male attraction when blended in too large amounts to the main compound. Both E8,Z10-dodecadien-1-ol, and E8,E10-dodecadienyl acetate have so far not been tested at the amounts present (ca. 3% and <1%, respectively) in sex pheromone glands of codling moth females.

Figure 2:
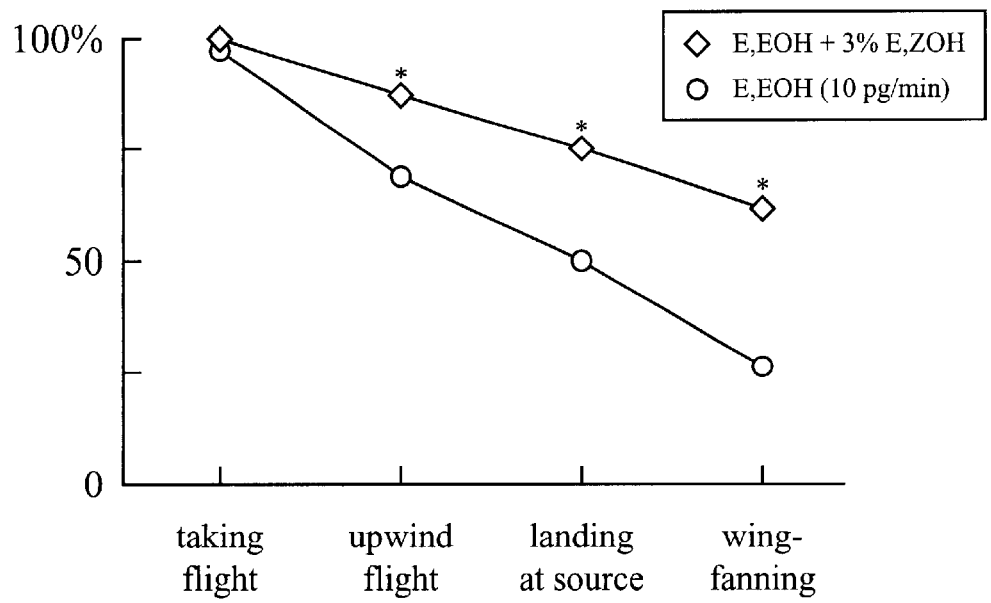
FIG. 2 shows the wind tunnel response of *C. pomonella* to E8,E10-dodecadien-1-ol with and without E8,Z10-dodecadien-1-ol.
Figure 3:
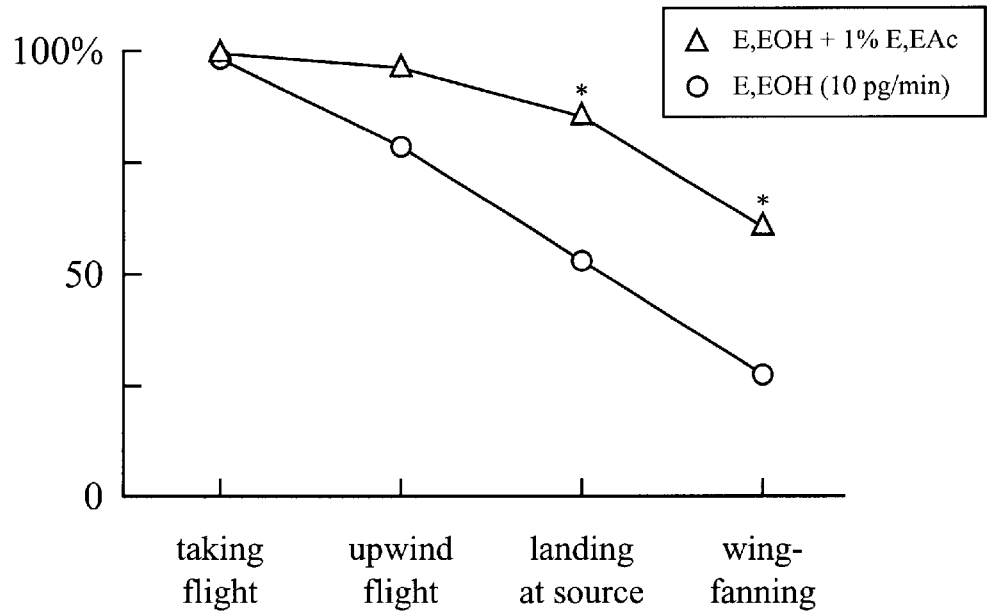
FIG. 3 shows the wind tunnel response of *C. pomonella* to E8,E10-dodecadien-1-ol with and without E8,E10-dodecadienyl acetate.

As evident from FIGS. 2 and 3, the combination of codlemone, E8,E10-dodecadien-1-ol, plus small amounts of E8,Z10-dodecadien-1-ol and E8,E10-dodecadienyl acetate has a superior effect on codling moth male attraction, and can thus be regarded to be more efficient for mating disruption and the attraction and killing technique than codlemone alone.

Wind Tunnel Experiments

Tests were done in a wind tunnel with a flight section of 63 by 90 by 200 cm. Dilutions of synthetic compounds in redistilled ethanol were released from an ultrasound evaporator (Gödde et al. 1999). A motor-driven syringe delivered pheromone solutions in ethanol, through micro-tubing, to a glass capillary tube with a 40 µm tip. A piezo-ceramic disc vibrates the tip of the capillary tube at 100–140 kHz, and the pheromone solution evaporates within a few cm of the tip of the capillary.

The main compound codlemone, E8,E10-dodecadien-1-ol, was applied at a rate of 10 pg/min, E8,Z10-dodecadien-1-ol was added at 3% by weight (FIG. 2), E8,E10-dodecadienyl acetate was added at 1% by weight (FIG. 3).

Test sessions started 1 h after lights off and lasted 3 to 4 h. Two-day-old males were placed individually in glass tubes (15 by 2.5 cm) stoppered with gauze, 15 min prior to testing. Males were released individually and were allowed 2 min to respond. Treatments were tested on 4 days with 15 males/day (n=60).

The sequence of male behaviours elicited by perception of sex pheromone includes activation from rest and taking flight, upwind-oriented flight towards the pheromone source, landing at the pheromone source, and display of courtship behaviors close to the source (walking while wingfanning) (FIGS. 2 and 3). These behaviors are followed by mating, if the pheromone source is a calling female.

The above combinations can also be supplemented with the use of one or more of the behaviour antagonists being the geometric isomers of delta8,delta10-dodecadien-1-yl acetate, as well as the use of one or more of the behavioral synergists of the group Z8-dodecen-1-yl acetate, E8-dodecen-1-yl acetate, Z10-dodecen-1-yl acetate and E10-dodecen-1-yl acetate.

The method for controlling codling moths by mating disruption or attraction and killing of the moths involves exposing the moths to the sex pheromone, E8,E10-dodecadien-1-ol, in combination with one or more behavioural antagonists, thereby controlling the codling moths. The behavioural antagonists may be E8,Z10-dodecadien-1-ol and/or E8,E10-dodecadienyl acetate. In one embodiment, E8,E10dodecadien-1-ol is present in a combination with E8,Z10-dodecadien-1-ol and/or E8,E10-dodecadienyl acetate in an amount of 100 parts by weight and 0.5–4 parts by weight, respectively, preferably 100 parts by weight and 1–3 parts by weight, respectively. In another embodiment E8,E10-dodecadien-1-ol is present in a combination with E8,Z10-dodecadien-1-ol in an amount of 100 parts by weight and 2–4 parts by weight, respectively. In a further embodiment, E8,E10-dodecadien-1-ol is present in a combination with E8,E10-dodecadienyl acetate in an amount of 100 parts by weight and 0.5–1 parts by weight, respectively. In an additional embodiment, the behaviour antagonist is one or more of the geometric isomers of delta8,delta10-dodecadien-1-yl acetate. In a further embodiment, the behavior synergist is one or more of the substances of the group Z8-dodecen-1-yl acetate, E8-dodecen1-yl acetate, Z10-dodecen-1-yl acetate and E10-dodecen-1-yl acetate.

Although the preferred embodiment of the method of the invention has been described above in some detail, it should be appreciated that a variety of embodiments will be readily apparent to one skilled in the art. The description of the method of this invention is not intended to be limiting to this invention, but is merely illustrative of the preferred embodiment.

REFERENCES

Arn, H, Guerin P. M. Buser, H-R, Rauscher S, Mani E (1985), "Sex pheromone blend of the codling moth, *Cydia pomonella:* evidence for a behavioural role of dodecan-1-ol. Experiemtia", 41:1482–1484.

Bengtssson M, Karg G, Kirsch P. A., Löfqvist J. Bauer A, WItzgall P (1994), "Mating disruption of pea moth *Cydia nigricana* F. (Lepidoptera: Tortricidae) by a repellent blend of sex pheromone and attraction inhibitors", J Chem Ecol 20,871–887.

Cardé, R T, Cardé A M, Hill A S, Roelofs. W L (1977), "Sex attractant specificity as a reproductive isolating method among the elbling species Archips argyrospillus and mortuanus and other sympatric tortricine moths (Lepidoptera: Tortricidae)", J Chem Ecol 3:71.84.

Charmillot N J, Hofer D (1297), "Control of codling moth, *Cydia pomonella L,* by an attract and kill formulation", IOBC wprs Bulletin Vol. 20(1),139–140.

Einhorn J, Beauvaie F, Gallois M, Desoolns C, Causee R (1984), "Constituants secondaires de la phéromone sexuelle du Carpocapse des Pommes, *Cydia pomonella* L. (Lepidoptera, Tortricidae)", C. R. Acad. Sc. Paris 299(III) :773–778.

El-Sayed A, Unelius R C, Liblikas I, Löfqvist J, Bengtsson M, Witzgall P (1990), "Effect of codlemone isomers on codling moth (Lepidoptera: Tortricidae) male attraction", Environ Entomol 27,1250–1254.

Gödde J., Arn, H., El-Sayed, A., (1999), "The pheromone sprayer, new technology in stimulus application", IOBC wprs Bulletin Vol. 22(9), 49–56.

Hathaway D O, McGovern T P, Beroza M, Moffitt H R, McDonough L M, Butt B A (1974), "An inhibitor of sexual attraction of male codling moth to a synthetic sex pheromone and virgin females in traps", Environ Entomol 3, 522–524.

Minke, Å. K., Cardé R T (1998), "Disruption of pheromone communication in moths; is the natural blend really most efficacious?", Entomol exp appl 49, 25–36.

Witzgall P, Bäckman A-C, Svensson M, Bengtsson M, Unelius C R, Vrkoc J, Kirsch P A, Ioriatti C, Löfqvist J (1996a), "Potential of a blend of E8,E10-12OH and E8,E10-12Ac for mating disruption of codling moth, *Cydia pomonella* L. (Lep., Tortricidae)", J Appl Entomol 120. 611–614.

Witzgall P, Chambon J-P, Bengtsson M, Unelius C R, Appelgren M, Makranczy G, Muralheedharan N, Reed D W, Hellrigl K, Buser H-R, Hallborg E, Bergström G, Toth M, Lövstedt C, Löfqvist J (1996b), "Sex pheromones and attractants in the Eucosmini and Grapholitini (Lepidoptera, Tortricidae)", Chemoecology 7,13–23.

We claim:

1. A method for controlling codling moths, *Cydia pomella,* comprising exposing codling moths to the sex pheromone, E8, E10-dodecadien-1-ol in combination with one or more behaviour antagonists selected from the geometric isomers of delta 8, delta 10-dodecadien-1-yl acetate.

2. The method according to claim 1, wherein the antagonist is present in an amount of less than 20% by weight relative to the pheromone.

3. The method according to claim 1, wherein the antagonist is present in an amount of about 1 to 5% by weight relative to the pheromone.

4. A method for inducing confusion in codling moths, *Cydia pomella,* comprising exposing codling moths to the sex pheromone, E8,E10-dodecadien-1-ol in combination with one or more behaviour antagonists selected from the geometric isomers of delta 8, delta 10-dodecadien-1-yl acetate.

5. The method according to claim 4, wherein the antagonist is present in an amount of less than 20% by weight relative to the pheromone.

6. The method according to claim 4, wherein the antagonist is present in an amount of about 1 to 5% by weight relative to the pheromone.

7. A method for controlling codling moths, *Cydia pomella,* comprising exposing codling moths to the sex pheromone, E8, E10dodecadien-1-ol in combination with one or more behaviour antagonists selected from the group consisting of Z8-dodecen-1-yl acetate, E8-dodecen-1-yl acetate, Z10-dodecen-1-yl acetate and E10-dodecen-1-yl acetate, wherein the antagonist is present in an amount of less than 20% by weight relative to the pheromone.

8. The method according to claim 7, wherein the antagonist is present in an amount of about 1 to 5% by weight relative to the pheromone.

9. A method for inducing confusion in codling moths, *Cydia pomella,* comprising exposing codling moths to the sex pheromone, E8,E10-dodecadien-1-ol in combination with one or more behaviour antagonists selected from the group consisting of Z8-dodecen-1-yl acetate, E8,-dodecen-1-yl acetate, Z10-dodecen-1-yl acetate and E10-dodecen-1-yl acetate, wherein the antagonist is present in an amount of less than 20% by weight relative to the pheromone.

10. The method according to claim 9, wherein the antagonist is present in an amount of about 1 to 5% by weight relative to the pheromone.

* * * * *